United States Patent [19]

Matolcsy et al.

[11] Patent Number: 4,846,883
[45] Date of Patent: Jul. 11, 1989

[54] SUCCINIC ACID DERIVATIVES AND PLANT GROWTH REGULATING COMPOSITIONS CONTAINING THEM

[75] Inventors: György Matolcsy; Gyula Kerekes, both of Budapest; Tamas Buban, Ujfehérfó ; Endre Vásárhelyi, Budapest; Magda, née Kálmán Kovács, Budapest; Iván Bélai, Budapest; Gerlei, Anikó, née Komáromy, Budapest, all of Hungary

[73] Assignee: Reanal Finomvegyszergyar, Budapest, Hungary

[21] Appl. No.: 18,903

[22] PCT Filed: Jun. 3, 1986

[86] PCT No.: PCT/HU86/00036
   § 371 Date: Jan. 30, 1987
   § 102(e) Date: Jan. 30, 1987

[87] PCT Pub. No.: WO86/07054
   PCT Pub. Date: Dec. 4, 1986

[30] Foreign Application Priority Data

Jun. 3, 1985 [HU] Hungary ................ 2142/85

[51] Int. Cl.$^4$ .................. A01N 37/00; C07C 69/40
[52] U.S. Cl. .................... 71/106; 560/193; 560/194
[58] Field of Search ............ 560/193, 194, 204; 71/106

[56] References Cited

U.S. PATENT DOCUMENTS

| | | | |
|---|---|---|---|
| 2,765,224 | 10/1956 | Lambrech | 560/193 X |
| 3,085,078 | 4/1963 | Fath | 560/194 X |
| 4,036,984 | 7/1977 | Takahashi et al. | 514/529 |
| 4,456,721 | 6/1984 | Halpern | 560/193 X |

*Primary Examiner*—Werren B. Lone
*Assistant Examiner*—Vera C. Clarke
*Attorney, Agent, or Firm*—Herbert Dubno; Jonathan Myers

[57] ABSTRACT

New succinic acid derivatives of the formula $$\begin{array}{l} CH_2-C(=O)-O-A \\ | \\ CH_2-C(=O)-O-A \end{array} \quad (I)$$

wherein
A represents hydrogen, a naphthoxyethyl group of formula (b), $$-CH_2-CH_2-O-\text{(naphthyl)} \quad (b)$$

or a substituted phenoxyethyl group of the formula $$-CH_2-CH(R)-O-\text{(phenyl with }R^1, R^2, R^3\text{)} \quad (a)$$

and in this latter formula
R stands for hydrogen or $C_{1-4}$ alkyl,
$R^1$ is hydrogen, halo or $C_{1-4}$ alkyl, and
$R^2$ and $R^3$ each stand for hydrogen or halo, and agriculturally acceptable salts thereof are prepared by reacting succinic anhydride with an aryloxyethanol of the formula $$HO-CH_2-CH(R)-O-A \quad (III)$$

The new succinic acid drivatives of the formula (I) possess plant growth regulating properties.

4 Claims, No Drawings

SUCCINIC ACID DERIVATIVES AND PLANT GROWTH REGULATING COMPOSITIONS CONTAINING THEM

The invention relates to new mono- or di-(aryloxyethyl)-succinates and plant growth regulating compositions containing these compounds. The invention also relates to a process for the preparation of new mono- or di-(aryloxyethyl)succinates.

Succinic acid-2,2-dimethyl-hydrazide (daminozide) is a well known compound utilized as active ingredient in plant growth regulating compositions (Alar-85 WP; see: Louis G. Nickell: Plant Growth Regulators Agricultural Uses; Springer Verlag, Berlin-Heidelberg-New York, 1982).

British patent specification No. 1,491,308 discloses various β-phenoxyethyl and β-phenylthioethyl carboxylates as fungicides; one of them being β-phenoxyethyl succinate.

Now it has been found that certain mono- and di-(aryloxyethyl)succinates and agriculturally acceptable salts thereof possess excellent plant growth regulating properties superior to those of the known substances of related structure.

Based on the above, the invention relates to mono- and di-(aryloxyethyl)succinates of the formula (I),

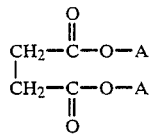

wherein
A represents hydrogen, a naphthoxyethyl group of formula (b),

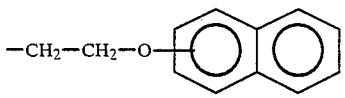

or a substituted phenoxyethyl group of the formula (a),

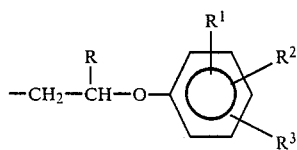

and in this latter formula
R stands for hydrogen or $C_{1-4}$ alkyl,
$R^1$ is hydrogen, halo or $C_{1-4}$ alkyl, and
$R^2$ and $R^3$ each stand for hydrogen or halo,
with the proviso that at least one of the two A groups is other than hydrogen,
and agriculturally acceptable salts thereof.

The invention also relates to agricultural, primarily plant growth regulating compositions, comprising as active agent at least one compound of the formula (I).

In the above formula the term "alkyl" means preferably methyl, whereas "halo" means preferably chloro. Substituents $R^1$, $R^2$ and $R^3$ are attached to the phenyl ring preferably in positions 2 and/or 4 and/or 5.

The invention also relates to a process for the preparation of compounds having the formula (I) with the exception of β-phenoxyethyl succinate.

The compounds of the formula (I) are prepared according to the invention by reacting succinic anhydride of formula (II)

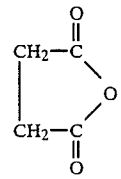

with an aryloxy ethanol of the formula (III),

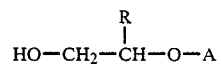

wherein A is as defined above.

Depending on whether a mono or a diester is required, the alcohol of the formula (III) is utilized in amounts of essentially 1 or 2 molar equivalents. The reaction is performed in the presence of a mineral acid, such as concentrated sulfuric acid, as catalyst.

The reaction is performed preferably in a solvent, such as in a chlorinated hydrocarbon (e.g. carbon tetrachloride), a ketone (e.g. methyl-ethyl ketone) or in a mixture thereof, or in an aromatic hydrocarbon (e.g. benzene).

Water formed in the diesterification reaction should be removed continuously from the system e.g. by utilizing a Marcusson apparatus.

The reaction temperature may be as high as the boiling point of the mixture. It is preferred to perform the reaction in a refluxing mixture.

The resulting product can be separated and, if necessary, purified by methods known per se.

The salts oof the monoesters may be salts formed with inorganic or organic bases, such as alkali metal salts, alkaline earth metal salts or salts formed with organic amines. These salts can be prepared by methods known per se.

Depending on whether a mono- or a diester is to be prepared, one proceeds e.g. as follows:

Succinic anhydride is suspended in carbon tetrachloride or in a mixture of carbon tetrachloride and methyl ethyl ketone, 1-2 drops of sulfuric acid are added to the suspension, the mixture is heated to reflux temperature, and one molar equivalent of the appropriate aryloxy alcohol of the formula (III) is added dropwise to the boiling suspension under stirring within one hour. Thereafter the mixture is stirred and refluxed for 1-3 hours. The mixture is allowed to cool, the separated monoester is filtered off, washed with water or aqueous alcohol, and dried at a temperature not exceeding 40° C.

When a diester is to be prepared, succinic anhydride, 2 molar equivalents of the appropriate aryloxy ethanol and 15-20 drops of sulfuric acid are added to an aromatic solvent, such as benzene. The mixture is stirred and refluxed for 5-15 hours in a flask equipped with a Marcusson apparatus. Thereafter the mixture is allowed to cool, the diester is filtered off, washed with water, aqueous sodium carbonate solution and then with water again, and dried at a temperature not exceeding 40° C.

The preparation of the compounds having the formula (I) is illustrated in detail in the following Examples.

EXAMPLE 1

(2-Methyl-2-(2',4',5'-trichlorophenoxy)-ethyl)succinate 16 g (0.16 mole) of finely powdered succinic anhydride are added to a mixture of 250 ml of dry carbon tetrachloride and 50 ml of methyl ethyl ketone. The mixture is heated to reflux, and a solution of 40.9 g (0.16 mole) of 2-methyl-2-(2',4',5'-trichlorophenoxy)-ethanol in 50 ml of methyl ethyl ketone is added dropwise to the stirred mixture within one hour. Thereafter the mixture is stirred and refluxed for one hour. The mixture is allowed to cool, the product is filtered off with suction, admixed with about 3 volumes of 80% aqueous methanol, and filtered. The product is dried at 40° C. 27.2 g (47.8%) of the title compound are obtained.

EXAMPLE 2

Di-(β-naphthoxyethyl)succinate 50 g (0.5 mole) of succinic anhydride, 188 g (1 mole) of β-naphthoxy-ethanol and 10 drops of concentrated sulfuric acid are added to 300 ml of dry benzene. The reaction mixture is stirred and refluxed for 8 hours under a Marcusson water separator. The mixture is allowed to cool, the separated product is filtered off by suction, washed with water, then three times with an aqueous sodium carbonate solution, and finally with water again. The product is dried at room temperature. 171 g (74.7%) of the title compound are obtained.

EXAMPLE 3

Phenoxyethyl succinate 250 g (2.5 moles) of finely powdered succinic anhydride and two drops of concentrated sulfuric acid are added to 300 ml of dry carbon tetrachloride. The mixture is heated to boiling, and then 345 g (2.5 moles) of phenoxyethanol are added dropwise to the stirred mixture within one hour. The resulting mixture is stirred under reflux for one hour, and then allowed to cool. The separated product is filtered off by suction, washed with water, and dried at room temperature. 583 g (98%) of the title compound are obtained.

The compounds of the formula (I) prepared according to the invention are summarized in Table I.

TABLE I

| Compound No. | A | R | $R^1$ | $R^2$ | $R^3$ | Mp. °C. | C=O (ester) | OH (acid) |
|---|---|---|---|---|---|---|---|---|
| 1 | H and (a) | H | H | H | H | 74–76 | 1725 | 3650–2400 |
| 2 | H and (a) | H | $CH_3$ | Cl | H | 81–82 | | |
| 3 | H and (a) | $CH_3$ | Cl | Cl | Cl | 160 | | |
| 4 | H and (b) | — | — | — | — | 114–116 | | |
| 5 | (a) and (a) | H | $CH_3$ | Cl | H | 79–80 | | |
| 6 | (b) and (b) | — | — | — | — | 138–138 | | |

(Characteristic IR bands, $cm^{-1}$)

The agricultural compositions according to the invention contain the active agents of the formula (I) in admixture with a solid or liquid carrier or diluent. The compositions may also coprise a surfactant and optionally other additives commonly used in agricultural practice.

The active agent content of the compositions may vary within 0.01 to 95% by weight, preferably 0.1 to 90% by weight.

The solid carriers or diluents usable according to the invention may be e.g. natural or synthetic mineral substances, such as silica, clay, talc, attapulgite, kaoline, calcium and aluminium silicates, calcium carbonate, dolomite, etc., furthermore solids of vegetable origin, e.g. sawdust, natural or synthetic resins, etc.

Of the liquid carriers or diluents the following are to be mentioned: aliphatic, aromatic, araliphatic or cyclic hydrocarbons, such as benzene, toluene, xylene, cyclohexanol and cyclohexanone, water, alcohols, such as isopropanol and glycol, mineral oil fractions, chlorinated hydrocarbons, ketones, such as acetone, methyl ethyl ketone, methyl isobutyl ketone, etc.

If the diluent is water, the composition according to the invention also comprises a surfactant.

The surfactants applicable according to the invention may be ionic or non-ionic emulsifying, dispersing or wetting agents. Preferred surfactants are polycondensates of ethylene oxide with fatty acid derivatives, polycondensates of ethylene oxide with alkylphenols or arylphenols, alkali metal or alkaline earth metal lignosulfonates, alkyl-aryl sulfonic acids, salts of sulfosuccinic esters and sucrose derivatives.

With respect to the appropriate selection of the surfactants reference is made to U.S. Pat. No. 3,713,804.

The compositions according to the invention can be formulated as solid or liquid products.

Of the solid compositions dusting powders, granulates, microgranulates and powdery compositions are to be mentioned. These solid compositions are utilized generally as such, without any further dilution.

Compositions prepared as liquids or to be applied in the liquid state are e.g. wettable powders, emulsifiable solutions and concentrates, suspendable powders and solutions. Of these compositions concentrates, emulsions and dispersions to be diluted with water are preferred.

Dusting powders contain generaly 0.1 to 5% of active ingredient in admixture with a carrier.

Granulates and microgranulates contain generally 0.5 to 10% by weight of active agent. These formulations are prepared by methods known per se, e.g. by impregnation techniques. Granular compositions may also comprise other additives, such as substances which control the release of active agent.

Wettable powders contain generally 20 to 95% by weight of active agent in admixture with a solid carrier and a surfactant, such as a wetting or dispersing agent.

Wettable powders are prepared by thoroughly admixing or grinding together the active agent and the additives. The resulting powder is easily wettable and suspendable and it can be diluted with water to any desired extent. The resulting aqueous compositions can be applied to the plants by spraying.

Emulsifiable concentrates or solutions contain generally 1 to 50 w/v% of an active agent together with a solvent, such as an aromatic hydrocarbon, and a surfactant, preferably an emulsifying agent. These compositions can be diluted with water to any desired extent before use.

Suspendable powders comprise the active agent in a very finely dispersed state as an oily or aqueous suspension from which the solid particles do not settle. Such compositions comprise generally 5 to 80% by weight of active agent.

These concentrated suspensions are prepared by grinding the active agent to a very fine powder and dispersing the resulting powder in a liquid carrier which also comprises the other additives. These suspensions can be diluted with water directly before use to any desired concentration.

Some characteristic compositions according to the invention are illustrated by the following Examples.

EXAMPLE I

Wettable powder

| (a) | Active agent No. 1 | 50% by weight |
| | Sodium lignosulfonate | 6 by weight |
| | Kaoline | 44 by weight |
| (b) | Active agent No. 2 | 50% by weight |
| | Sodium lignosulfonate | 5 by weight |
| | Isopropyl naphthalene sulfonate | 1 by weight |
| | Talc | 44 by weight |
| (c) | Active agent No. 1 | 90% by weight |
| | Sodium dioctyl sulfosuccinate | 0.2 by weight |
| | Synthetic silica | 9.8 by weight |
| (d) | Active agent No. 4 | 80% by weight |
| | Sodium alkyl naphthalene sulfonate | 4 by weight |
| | Methyl cellulose | 2 by weight |
| | Kieselguhr | 14% by weight |

EXAMPLE II

Emulsifiable concentrate

| (a) | Active agent No. 1 | 250 g |
| | Condensate of ethylene oxide with alkyl phenol | 30 g |
| | Calcium alkylaryl sulfonate | 50 g |
| | Mineral oil fraction (bp.: 160–190° C.) | 670 g |
| (b) | Active agent No. 3 | 400 g |
| | Condensate of ethylene oxide with alkyl phenol | 60 g |
| | Sodium alkylaryl sulfonate | 40 g |
| | Cyclohexanone | 150 g |
| | Xylene | 400 g |
| (c) | Active agent No. 5 | 400 g |
| | Condensate of ethylene oxide with tri-styryl phenol phosphate | 50 g |
| | Cyclohexanone | 400 g |
| | Sodium alkyl benzene sulfonate | 40 g |

EXAMPLE III

Suspendable concentrate

| Active agent No. 5 | 500 g |
| Condensate of ethylene oxide with tristyryl phenol phosphate | 50 g |
| Condensate of ethylene oxide with alkyl phenol | 50 g |
| Polycarboxylic acid sodium salt | 20 g |
| Ethylene glycol | 50 g |
| Polysaccharide | 1.5 g |
| Water | 320 g |

EXAMPLE IV

Granulate

| Active agent No. 1 | 50 g |
| Propylene glycol | 25 g |
| Vegetable oil | 50 g |
| Granular clay (diameter: 0.2–0.6 mm) | 950 g |

The activity of the plant growth regulating compositions according to the invention was tested under both greenhouse and field conditions.

A wettable powder of 50% by weight active agent content was prepared by admixing the active agent in question with 40% by weight of kaoline and 10% by weight of a fatty alcohol sulfonate. The resulting wettable powder was diluted with water before use to the desired concentration.

Lettuce and cucumber seeds were dressed by wetting them thoroughly with suspensions of varying active agent content. The dressed seeds were dried at room temperature for 48 hours and then germinated in Petri dishes on filter paper. Stem and root lengths were measured on the 12th day for cucumber and on the 8th day for lettuce, and the data were compared to those of controls treated in the same way with distilled water. The results (stimulation or suppression) are summarized in Tables II and III.

Plant growth regulating and damaging effects were also tested on beans under greenhouse conditions. Young bean plants grown in pots were treated in the two true leaves stage with 5 ml of spray solution per plant, containing varying amounts of active agents. 3 weeks after treatment the effects exerted on internodium length and growth stage were assessed and compared to those observed on untreated controls. The results, expressed as percentages in relation to untreated controls, are listed in Tables IV and V. The phytotoxic effects were also evaluated.

The data of Tables II to V indicate that the compositions according to the invention exert growth retarding effects on the plants tested. The compositions significantly reduce stem and root growth in relation to the untreated controls, and also significantly reduce internodial length. The stem and plant growth retarding effects of the compositions are at least identical to or even greater than those exerted by compositions comprising as active agent succinic acid-2,2-dimethyl-hydrazide, a known plant growth regulating compound. The compositions according to the invention have no phytotoxic effects.

The effects exerted on vegetative growth, flowering and crop yield were examined in three years' small parcel field tests on young (2–4 years old) apple trees. Apple tree varieties Gloster/M.9 and Starking Nm/N.9 of strong or medium growth, respectively, were tested.

The apple trees were sprayed until dripping with spray solutions containing varying amounts of active agents at the period of intense shooting. The trees were treated twice with a hand-operated spraying apparatus.

The lengths of two main shoots (predicted as having the strongest growth), each, were measured on every tree, the nodes were counted, and the individual shoots were marked prior to treatment. These shoots were measured twice again at a later phenophasis of plant growth. At the end of the vegetative period, one skeletal branch was selected on each of the treated and control trees. The circumferences of the branches and the lengths of the shoots shorter than 10 cm, to be regarded as potentially fructiferous parts, were measured.

The effects exerted on shoot growth and growth properties were evaluated in relation to untreated controls (Tables VI and VII).

The data of Tablee VI indicate that phenoxyethyl succinate, in a higher dosage, considerably decreases the shoot growth on young trees. According to the data, the final shoot length (70.1 cm) was only 81.4% of that measured on untreated trees. From the time of the first treatment to the end of vegetation period the total shoot growth measured on treated trees was 34.2 cm in average, which, compared to the average value of 53.6 cm measured on untreated plants, represents a decrease of 36.2%.

When applied in a smaller dosage, phenoxyethyl succinate has a shoot growth reducing effect of the same order as succinic acid-2,2-dimethyl-hydrazide, a known very effective plant growth reducing agent. It has been observed that on apple varieties of medium growth the number of fructiferous parts related to branch circumference increases significantly upon treating the trees with the compositions according to the invention (see Table VII).

In the young apple plantation treated according to the invention the effects exerted on flowering and crop yield were examined in the year following the year of treatment. The results are shown in Table VIII.

The data of Table VIII indicate that the compositions according to the invention significantly promote bud formation, and the extent of flowering (number of flowers/1 cm of branch circumference) remarkably exceeds that observed on the untreated controls.

Due to the stimulation of flowering, the compositions according to the invention also increase crop yield to a great extent. Related to the untreated controls, an increase of 32% in crop yield can be observed on Gloster apple variety and that of 13-18% on Starking variety, which represent a surplus of 2 tons/hectare in a 3 years plantation and a surplus of 2.7 tons/hectare in a 5 years plantation.

The efficiency of plant growth regulating activity can be increased when the active agent is applied in greater amounts (0.4% by volume) and in combination with 2-chloroethyl phosphonic acid.

The frost resistance of apple twigs was examined by their electrolytic conductivity measured after freezing in a cryostate. It has been observed that the frost resistance of twigs obtained from trees treated according to the invention is the same as, or sometimes even better than, that of the untreated ones.

The new compositions according to the invention were also tested under small parcel field conditions on Pándy variety morello trees of low productivity. The trees were sprayed until dripping once in the flowering period. It was observed that the new compositions according to the invention significantly increase fruit fixation. Compared to the results obtained after a treatment with an N-phenyl-phthalamic acid containing known composition, the crop yield increases by 50%; and the increase in crop yield is about twofold in comparison with the untreated controls. Despite this extremely great increase in crop yield, the average dimensions of the fruits do not decrease.

Phenoxyethyl succinate exerts a favorable influence on the growth characteristics of young apple trees, which can be attributed to the reduction of shoot growth and the stimulation of flower bud formation. As a consequence, the crop yield can be increased and the productive stage can be attained in an earlier age.

With morello trees of low productivity, the improvement of fruit fixation and the extremely high increase in crop yield are significantly advantageous results.

The compositions according to the invention may also contain, beside the compounds of the formula (I), other known plant regulating agents, furthermore plant protecting agents, such as herbicides, fungicides, bactericides and insecticides, as well as antidotes.

The invention also relates to a process for regulating plant growth, according to which plants are treated with an effective amount of a compound of the formula (I) or with a composition containing such a compound.

TABLE II

| | | | Cucumber | | | |
|---|---|---|---|---|---|---|
| Active agent | Concentration % by weight | Amount g/100 kg of seed | cm | Root length % increases related to the control | cm | Stem length % increases related to the control |
| Phenoxyethyl succinate | 0.12 | 48 | 10.2 | +7.4 | 4.2 | −19.3 |
| | 0.06 | 24 | 8.6 | −9.5 | 3.9 | −25.0 |
| | 0.05 | 20 | 8.1 | −14.8 | 4.7 | −9.7 |
| | 0.04 | 16 | 7.7 | −18.9 | 5.3 | +1.9 |
| Control (treated with water) | — | — | 9.5 | — | 5.2 | — |

TABLE III

| | Lettuce | | |
|---|---|---|---|
| Active agent | Concentration, ppm | Stem length cm | % increase related to the control |
| Phenoxyethyl succinate | 10 | 1.6 | −20 |
| | 100 | 1.3 | −35 |
| | 1000 | 1.1 | −45 |
| β-Naphthoxy-ethyl succinate | 10 | 1.7 | −15 |
| | 100 | 1.5 | −25 |
| | 1000 | 1.3 | −35 |
| (2-(4'-Chloro-2'-methyl-phenoxy)-ethyl) succinate | 10 | 1.6 | −20 |
| | 100 | 0.8 | −60 |
| | 1000 | 0.3 | −85 |
| 2-Methyl-2-(2',4',5'-trichlorophenoxy)-ethyl succinate | 10 | 1.7 | −15 |
| | 100 | 1.0 | −50 |
| | 1000 | 0.2 | −90 |
| Succinic acid-2,2-dimethylhydrazide (known compound) | 10 | 1.5 | −25 |
| | 100 | 0.6 | −70 |
| | 1000 | 0.4 | −80 |
| Control (treated with water) | — | 2.0 | — |

TABLE IV

| Active agent | Concentration, % by wt. | Beans Plant height, cm | Number of nodes | Internodium length cm | % increase related to the control | Phytotoxicity % |
|---|---|---|---|---|---|---|
| Phenoxyethyl succinate | 0.01 | 15.0 | 3 | 3.0 | −26.8 | 0.0 |
| | 0.05 | 14.5 | 2 | 2.3 | −41.5 | 0.0 |
| | 0.1 | 13.5 | 2 | 2.2 | −46.4 | 0.0 |
| | 0.5 | 12.6 | 1 | 2.1 | −48.8 | 0.0 |
| Control (untreated) | — | 18.5 | 4 | 4.1 | — | — |

TABLE V

| Active agent | Application rate kg/hectare | Beans Height, cm | % increase related to the control | Phytotoxicity % |
|---|---|---|---|---|
| Phenoxyethyl succinate | 0.06 | 7.0 | −16.7 | 0.0 |
| | 0.6 | 5.5 | −34.6 | 0.0 |
| β-Naphthoxy-ethyl succinate | 0.06 | 8.0 | −4.8 | 0.0 |
| | 0.6 | 5.0 | −40.5 | 0.0 |
| 2-(4'-Chloro-2'-methyl-phenoxy)-ethyl succinate | 0.06 | 7.0 | −16.7 | 0.0 |
| | 0.6 | 6.0 | −28.6 | 0.0 |
| 2-Methyl-2-(2',4',5'-tri-chloro-phenoxy)-ethyl succinate | 0.06 | 4.7 | −44.1 | 0.0 |
| | 0.6 | 3.4 | −59.6 | 0.0 |
| Succinic acid-2,2-dimethyl-hydrazide (known compound) | 0.06 | 5.0 | −40.5 | 0.0 |
| | 0.6 | 4.5 | −46.6 | 0.0 |
| Control (untreated) | — | 8.4 | — | — |

TABLE VI

| | | Apple (Gloster variety) | | | | | | |
|---|---|---|---|---|---|---|---|---|
| Active agent | Concentration, % by weight | Growth 08.06–07.23 Shoot length, cm | No. of nodes | Inter-* nodium length mm | Growth 07.23–10.05 Shoot length, cm | No. of nodes | Inter-* nodium length mm | Final length of shoots 10.05 |
| Phenoxyethyl succinate | 0.4 | 19.7 | 10.6 | 18.6 | 14.5 | 9.3 | 15.6 | 70.1 |
| Control (untreated) | — | 28.3 | 14.0 | 20.2 | 25.3 | 13.4 | 18.9 | 86.1 |

*Measured at the end of the examination period

TABLE VII

| Active agent | Concentration, % by weight | Apple (Starking variety) Average shoot length, cm | % increase related to the control | Productive part/ branch circumference, cm | % increase related to the control |
|---|---|---|---|---|---|
| Phenoxyethyl succinate | 0.2 | 23.4 | −13.1 | 6.5 | +38.2 |
| Succinic acid-2,2-dimethyl-hydrazide (known compound) | 0.3 and 0.15 | 23.4 | −13.1 | 3.8 | −19.2 |
| Control (untreated) | — | 26.9 | — | 4.7 | — |

TABLE VIII

| Active agent | Concentration, % by weight | Apple (var. Gloster) No. of flowers/ branch circumference, cm | Crop yield kg/tree | Apple (var. Starking) No. of flowers/ branch circumference, cm | Crop yield kg/tree |
|---|---|---|---|---|---|
| Phenoxyethyl succinate | 0.4 | 3.6 | 8.6 | — | — |
| Phenoxyethyl succinate | 0.2 | — | — | 8.2 | 23.1 |
| Succinic acid-(2,2-dimethyl-hydrazide) + 2-chloroethyl phosphonic acid | 0.3 + 0.06 | 3.7 | 8.8 | — | — |
| Phenoxyethyl succinate + 2-chloroethyl phosphonic acid | 0.2 + 0.06 | — | — | 8.1 | 24.1 |

TABLE VIII-continued

| Active agent | Concentration, % by weight | Apple (var. Gloster) | | Apple (var. Starking) | |
|---|---|---|---|---|---|
| | | No. of flowers/ branch circumference, cm | Crop yield kg/tree | No. of flowers/ branch circumference, cm | Crop yield kg/tree |
| Control (untreated) | — | 3.0 | 6.6 | 5.9 | 20.4 |

TABLE IX

| Active agent | Concentration, % by weight | Morello | | | |
|---|---|---|---|---|---|
| | | No. of fruits/ 100 flowers | Fruit diameter mm | Fruit weight g | Crop yield kg/tree |
| Phenoxyethyl succinate | 0.04 | 27 | 23.4 | 6.12 | 38.4 |
| N—phenyl-phthalamic acid (known compound) | 0.12 | 19 | 23.4 | 6.28 | 25.8 |
| Control (untreated) | — | 20 | 23.5 | 6.37 | 21.2 |

What we claim is:

1. A compound selected from the group consisting of:
(a) beta-naphthyloxyethyl succinate;
(b) 2-(4'-chloro-2'-methyl-phenoxy)-ethyl succinate; and
(c) di-[2-(4'-chloro-2'-methyl-phenoxy)-ethyl]succinate;
or an agriculturally acceptable salt thereof.

2. The compound defined in claim 1 which is 2-(4'-chloro-2'-methyl-phenoxy)-ethyl succinate; or an agriculturally acceptable salt thereof.

3. A plant growth regulating composition which comprises as active ingredient a plant growth regulating effective amount of the compound defined in claim 1 or an agriculturally acceptable salt thereof together with an agriculturally acceptable inert carrier.

4. A method of decreasing shoot and root length while at the same time increasing flowering and yield in a crop which comprises the step of applying to the locus of the crop a plant growth regulating amount of the compound defined in claim 1; or an agriculturally acceptable salt thereof.

* * * * *